US006949548B2

(12) United States Patent
Pöder et al.

(10) Patent No.: US 6,949,548 B2
(45) Date of Patent: Sep. 27, 2005

(54) COMBINATION THERAPY FOR THE TREATMENT OF HEART FAILURE

(75) Inventors: Pentti Pöder, Espoo (FI); Heimo Haikala, Espoo (FI)

(73) Assignee: Orion Corporation, Espoo (FI)

( * ) Notice: Subject to any disclaimer, the term of this patent is extended or adjusted under 35 U.S.C. 154(b) by 0 days.

(21) Appl. No.: 10/482,692

(22) PCT Filed: Jul. 4, 2002

(86) PCT No.: PCT/FI02/00606

§ 371 (c)(1),
(2), (4) Date: Jun. 8, 2004

(87) PCT Pub. No.: WO03/007962

PCT Pub. Date: Jan. 30, 2003

(65) Prior Publication Data

US 2004/0209885 A1 Oct. 21, 2004

(30) Foreign Application Priority Data

Jul. 4, 2001  (FI) .............................................. 20011464

(51) Int. Cl.⁷ ........................ A61K 31/50; A61K 31/40; A61K 31/165; A61K 31/135
(52) U.S. Cl. ........................ 514/247; 514/411; 514/620; 514/651; 514/653
(58) Field of Search ................................ 514/247, 411, 514/620, 651, 653

(56) References Cited

FOREIGN PATENT DOCUMENTS

| WO | WO 92/12135 A | 7/1992 |
| WO | WO 98/58638 A | 12/1998 |

OTHER PUBLICATIONS

John G.F. Cleland et al., "Levosimendan: a new era for inodilator therapy for heart failure?," Current Opinion in Cardiology, vol. 17, No. 3, pp. 257–265, May 2002.

Heimo Haikala et al., "The role of cAMP– and cGMP–dependent protein kinases in the cardiac actions of the new calcium sensitizer, levosimendan," Cardiovascular Research, vol. 34, No. 3, 1997, pp. 536–546.

Katalin György et al., "Haemodynamic effects of intravenous levosimendan during oral metroprolol treatment in anesthetized dogs," Journal of Molecular and Cellular Cardiology, vol. 29, No. 5, 1997, p. A127, col. Sa 81.

David P. Figgitt et al., "Levosimendan", Drugs, vol. 61, No. 5, Mar. 2001, pp. 613–627.

A. Lochner et al., "Effect of a Calcium–Sensitizing Agent, Levosimendan, on the Postcardioplegic Inotropic Response of the Myocardium," Cardiovascular Drugs and Therapy, vol. 14, No. 3, 2000, pp. 271–281.

Nicolai Gruhn et al., "Coronary Vasorelaxant Effect of Levosimendan, a New Inodilator with Calcium–Sensitizing Properties," Journal of Cardiovascular Pharmacology, vol. 31, No. 5, 1998, pp. 741–749.

Mara T. Slawsky, MD, PhD. et al., "Acute Hemodynamic and Clinical Effects of Levosimendan in Patients with Severe Heart Failure," Circulation, vol. 102, No. 18, 2000, pp. 2222–2227.

*Primary Examiner*—Raymond J. Henley, III
(74) *Attorney, Agent, or Firm*—Finnegan, Henderson, Farabow, Garrett & Dunner, LLP

(57) ABSTRACT

A combination therapy for the treatment of heart failure comprises administering a combination of levosimendan or a pharmaceutically acceptable salt thereof and a beta-adrenergic receptor antagonist to a patient. The combination synergistically reduces mortality in heart failure patients.

10 Claims, No Drawings

COMBINATION THERAPY FOR THE TREATMENT OF HEART FAILURE

This application is a U.S. national stage filing of PCT International Application No. PCT/FI02/00606, filed on Jul. 4, 2002, which claims the benefit of priority to Finnish patent application no. 2001164, filed on Jul. 4, 2001.

TECHNICAL FIELD

The present invention relates to a method for the treatment of heart failure by administering a synergistic combination of levosimendan or a pharmaceutically acceptable salt thereof and a beta-adrenergic receptor antagonist to a patient in need of such treatment. The invention also relates to a medical product comprising levosimendan or a pharmaceutically acceptable salt thereof and a beta-adrenergic receptor antagonist as a combined preparation.

BACKGROUND OF THE INVENTION

Levosimendan, which is the (−)-enantiomer of [[4-(1,4,5,6-tetrahydro-4-methyl-6-oxo-3-pyridazinyl)phenyl]hydrazono]propanedinitrile, and the method for its preparation is described in EP 565546 B1. Levosimendan is potent in the treatment of heart failure and has significant calcium dependent binding to troponin. Levosimendan is represented by the formula:

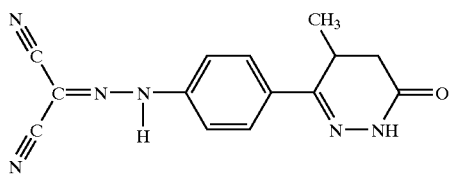

The hemodynamic effects of levosimendan in man are described in Sundberg, S. et al., Am. J. Cardiol., 1995; 75: 1061–1066 and in Lilleberg, J. et al., J. Cardiovasc. Pharmacol., 26(Suppl.1), S63–S69, 1995. Pharmacokinetics of levosimendan in man after i.v. and oral dosing is described in Sandell, E.-P. et al., J. Cardiovasc. Pharmacol., 26(Suppl.1), S57–S62, 1995. The use of levosimendan in the treatment of myocardial ischemia is described in WO 93/21921. The use of levosimendan in the treatment of pulmonary hypertension is described in WO 99/66912. Clinical studies have confirmed the beneficial effects of levosimendan in congestive heart failure patients.

A method for treating heart failure by administering an inotropic phosphoesterase inhibitor such as enoximone or vesnarinone together with a beta-adrenergic receptor antagonist is described in patent publication WO 98/58638.

SUMMARY OF THE INVENTION

It has now been found that administration of levosimendan together with a beta-adrenergic receptor antagonist, has a beneficial synergistic effect on the mortality as well as the hemodynamic function of congestive heart failure patients. Therefore, the combination is particularly useful for the treatment of heart failure, including acute and chronic heart failure.

Thus, in one aspect the present invention provides a method for the treatment of heart failure, said method comprising administering to a patient in need thereof levosimendan or a pharmaceutically acceptable salt thereof in combination with a beta-adrenergic receptor antagonist.

In another aspect the invention provides a method for reducing mortality of heart failure patients, said method comprising administering to a patient in need thereof levosimendan or a pharmaceutically acceptable salt thereof in combination with a beta-adrenergic receptor antagonist.

In another aspect the invention provides a medical product comprising, separately or together, as active ingredients levosimendan or a pharmaceutically acceptable salt thereof and a beta-adrenergic receptor antagonist as a combined preparation.

In another aspect invention provides a pharmaceutical composition comprising as active ingredients levosimendan or a pharmaceutically acceptable salt thereof and a beta-adrenergic receptor antagonist.

In another aspect the invention provides the use of levosimendan or a pharmaceutically acceptable salt thereof and a beta-adrenergic receptor antagonist as active ingredients in the manufacture of a combined preparation for simultaneous, separate or sequential administration.

In still another aspect the invention provides use of levosimendan or a pharmaceutically acceptable salt thereof and a beta-adrenergic receptor antagonist as active ingredients in the manufacture of a medicament for reducing mortality of heart failure patients.

DETAILED DESCRIPTION

The method of the invention relates to a combination therapy for the treatment of heart failure, particularly reducing mortality of heart failure patients, by administering to a patient in need thereof as active ingredients levosimendan or a pharmaceutically acceptable salt thereof and a beta-adrenergic receptor antagonist.

The active ingredients may be administered simultaneously, separately or sequentially. In particular, the method comprises administering to a patient an amount of active ingredients or combination thereof which is effective to reduce mortality of the patient. Preferably, the method comprises administering to a patient a synergistically effective amount of the combination. The administration routes of the active ingredients include, but are not limited to, enteral, e.g. oral or rectal, or parenteral, e.g. intravenous, intramuscular, intraperitoneal or transdermal. In the treatment of acute heart failure, the active ingredients are preferably administered parenterally, intravenous route being particularly preferred. In the treatment of chronic heart failure, oral route is particularly preferred.

Levosimendan may be administered e.g. intravenously using an infusion rate which is from about 0.01 to 10 µg/kg/min, preferably from about 0.02 to 5 µg/kg/min, typically from about 0.05 to 0.4 µg/kg/min. For an intravenous bolus a suitable dose is in the range from about 1 to 200 µg/kg, preferably from about 2 to 100 µg/kg, typically from about 5 to 30 µg/kg. For the treatment of acute heart failure an intravenous bolus followed by continuous infusion may be needed.

Levosimendan may be administered orally to man in daily dose ranging from about 0.1 to 20 mg, preferably from 0.2 to 15 mg, more preferably from 0.5 to 10 mg, given once a day or divided into several doses a day, depending on the age, body weight and condition of the patient. The effective amount of levosimendan to be administered to a subject depends upon the condition to be treated, the route of administration, age, weight and the condition of the patient.

Various beta-adrenergic receptor antagonists, also called beta-blockers, are currently in clinical use for eliminating the harmful chronic myocardial stimulation which is caused by failing heart. Preferred beta-adrenergic receptor antagonists include metoprolol, carvedilol, atenolol, propranolol, acebutolol, betaxolol, nadolol, talinolol or a pharmaceutically acceptable salt thereof.

Particularly preferred beta-adrenergic receptor antagonists to be used in the present invention are metoprolol and carvedilol or a pharmaceutically acceptable salt thereof.

According to the invention, a beta-adrenergic receptor antagonist may be administered in daily doses, which are clinically accepted for such agents. For example, a suitable daily dose of metoprolol as a tartrate or succinate salt, is about 100–200 mg and for carvedilol about 5–50 mg depending upon the condition to be treated, the route of administration, age, weight and the condition of the patient.

The combination may be supplemented with one or more other active ingredients.

The active ingredients or the combination thereof may be administered periodically, e.g. weekly or biweekly, or daily or several times a day, depending on the patient's needs.

The active ingredients can be formulated into pharmaceutical dosage forms suitable for the treatment according to the present invention using the principles known in the art. They are given to a patient as such or preferably in combination with suitable pharmaceutical excipients in the form of tablets, dragees, capsules, suppositories, emulsions, suspensions or solutions whereby the contents of the active compound in the formulation is from about 0.5 to 100% per weight. Choosing suitable ingredients for the composition is a routine for those of ordinary skill in the art. It is evident that suitable carriers, solvents, gel forming ingredients, dispersion forming ingredients, antioxidants, colours, sweeteners, wetting compounds, release controlling components and other ingredients normally used in this field of technology may be also used.

The active ingredients may be formulated in the same pharmaceutical formulation. Alternatively, the active ingredients are formulated as separate pharmaceutical dosage forms. The combination of the two pharmaceutical dosage forms may be packed as a single medical product or kit for use in the method of the invention.

Formulations suitable for intravenous administration such as injection or infusion formulation, comprise sterile isotonic solutions of the active ingredient and vehicle, preferably aqueous solutions. Typically an intravenous infusion solution of levosimendan comprises from about 0.01 to 0.1 mg/ml of levosimendan. Typical intravenous solution of metoprolol comprises about 1 mg/ml of metoprolol. The pharmaceutical formulation may be also in the form of an intravenous infusion concentrate to be diluted with an aqueous vehicle before use. Such concentrate may comprise as a vehicle a pharmaceutically acceptable organic solvent such as dehydrated ethanol.

For oral administration of the active ingredients in tablet form, suitable carriers and excipients include e.g. lactose, corn starch, magnesium stearate, calcium phosphate and talc. For oral administration in capsule form, useful carriers and excipients include e.g. lactose, corn starch, magnesium stearate and talc. For controlled release oral compositions release controlling components can be used. Typical release controlling components include hydrophilic gel forming polymers such as hydroxypropylmethyl cellulose, hydroxypropyl cellulose, carboxymethyl celluloses, alginic acid or a mixture thereof; vegetable fats and oils including vegetable solid oils such as hydrogenated soybean oil, hardened castor oil or castor seed oil (sold under trade name Cutina HR), cotton seed oil (sold under the trade names Sterotex or Lubritab) or a mixture thereof; fatty acid esters such as triglycerides of saturated fatty acids or their mixtures e.g. glyceryl tristearates, glyceryl tripalmitates, glyceryl trimyristates, glyceryl tribehenates (sold under the trade name Compritol) and glyceryl palmitostearic acid ester.

Tablets can be prepared by mixing the active ingredient with the carriers and excipients and compressing the powdery mixture into tablets. Capsules can be prepared by mixing the active ingredient with the carriers and excipients and placing the powdery mixture in capsules, e.g. hard gelatin capsules. Typically a tablet or a capsule comprises from about 0.1 to 10 mg, more typically 0.2 to 5 mg, of levosimendan or/and from about 20 to 200 mg of metoprolol.

The beta-adrenergic receptor antagonists may be included in the levosimendan formulation or may be formulated separately as described above using principles well known in the art.

Salts of levosimendan may be prepared by known methods. Pharmaceutically acceptable salts are useful as active medicaments, however, preferred salts are the salts with alkali or alkaline earth metals.

EXAMPLES

Pharmaceutical examples.

Example 1

Concentrate Solution for Intravenous Infusion

| | |
|---|---|
| (a) levosimendan | 2.5 mg/ml |
| (b) Kollidon PF12 | 10 mg/ml |
| (c) citric acid | 2 mg/ml |
| (d) dehydrated ethanol | ad 1 ml (785 mg) |

The concentrate solution was prepared by dissolving citric acid, Kollidon PF121 and levosimendan to dehydrated ethanol in the sterilized preparation vessel under stirring. The resulting bulk solution was filtered through a sterile filter (0.22 μm). The sterile filtered bulk solution was then aseptically filled into 8 ml and 10 ml injection vials (with 5 ml and 10 ml filling volumes) and closed with rubber closures.

The concentrate solution for intravenous infusion is diluted with an aqueous vehicle before use. Typically the concentrate solution is diluted with aqueous isotonic vehicles, such as 5% glucose solution or 0.9% NaCl solution so as to obtain an aqueous intravenous solution, wherein the amount of levosimendan is generally within the range of about 0.001–1.0 mg/ml, preferably about 0.01–0.1 mg/ml.

Example 2

| Hard gelatin capsule size 3 | |
|---|---|
| Levosimendan | 2.0 mg |
| Lactose | 198 mg |

The pharmaceutical preparation in the form of a capsule was prepared by mixing levosimendan with lactose and placing the powdery mixture in hard gelatin capsule.

Example 3

| Hard gelatin capsule size 3 | |
|---|---|
| Metoprolol tartrate | 100.0 mg |
| Lactose | 198 mg |

Experiments

Effect of the Combination on the Mortality of Heart Failure Patients

A 6-hour infusion of levosimendan using a bolus of 6, 12 or 24 μg/kg and subsequent infusion of 0.1, 0.2 or 0.4 μg/kg/min was given to heart failure patients with or without concomitant use of a beta-blocker. The 72-hour, 14-day and 180 day mortality was measured. The results are shown in Table 1. It can be seen that the combination provided synergistic reduction in the mortality of the heart failure patients.

TABLE 1

The mortality of patients receiving levosimendan, a beta-blocker or a combination thereof.

| | Received beta-blocker | | | | | Did not receive beta-blocker | | | | |
|---|---|---|---|---|---|---|---|---|---|---|
| Event | Placebo (N = 42) | LS 6 + 0.1 (N = 43) | LS 12 + 0.2 (N = 38) | LS 24 + 0.2 (N = 32) | LS 24 + 0.4 (N = 42) | Placebo (N = 60) | LS 6 + 0.1 (N = 60) | LS 12 + 0.2 (N = 62) | LS 24 + 0.2 (N = 67) | LS 24 + 0.4 (N = 57) |
| | | | n(%) | | | | | n(%) | | |
| 72-hour mortality | 3(7.1%) | 1(2.3%) | 2(5.3%) | 0(0.0%) | 0(0.0%) | 7(11.7%) | 5(8.3%) | 1(1.6%) | 5(7.5%) | 5(8.8%) |
| 14-day mortality | 6(14.3%) | 4(9.3%) | 4(10.5%) | 3(9.4%) | 2(4.8%) | 14(23.3%) | 9(15.0%) | 5(8.1%) | 10(14.9%) | 9(15.8%) |
| 180-day mortality | 15(35.7%) | 13(30.2%) | 10(26.3%) | 12(37.5%) | 10(23.8%) | 31(51.7%) | 30(50.0%) | 25(40.3%) | 31(46.3%) | 26(45.6%) |

What is claimed is:

1. A medical product comprising, separately or together, as active ingredients levosimendan or a pharmaceutically acceptable salt thereof and a beta-adrenergic receptor antagonist as a combined preparation, wherein the active ingredients are present in a combined amount effective for the treatment of heart failure.

2. A pharmaceutical composition comprising as active ingredients levosimendan or a pharmaceutically acceptable salt thereof and a beta-adrenergic receptor antagonist, wherein the active ingredients are present in a combined amount effective for the treatment of heart failure.

3. A composition according to claim 2, which is adapted for oral administration.

4. A composition according to claim 3, which is in the form of a tablet or capsule.

5. A composition according to claim 3, comprising from 0.1 to 10 mg of levosimendan.

6. A composition according to claim 4, comprising from 0.1 to 10 mg of levosimendan.

7. A composition according to claim 5, comprising from 0.2 to 5 mg of levosimendan.

8. A composition according to claim 6, comprising from 0.2 to 5 mg of levosimendan.

9. A method for the treatment of heart failure, said method comprising administering to a patient in need thereof levosimendan or a pharmaceutically acceptable salt thereof in combination with a beta-adrenergic receptor antagonist.

10. A method for reducing mortality of a heart failure patient, said method comprising administering to a patient in need thereof levosimendan or a pharmaceutically acceptable salt thereof in combination with a beta-adrenergic receptor antagonist.

* * * * *